United States Patent [19]

Dietz et al.

[11] Patent Number: 5,417,987
[45] Date of Patent: May 23, 1995

[54] METHOD FOR CONTROLLING BIVALVES SUCH AS ZEBRA MUSSELS

[75] Inventors: Thomas H. Dietz; John W. Lynn; Harold Silverman, all of Baton Rouge, La.

[73] Assignees: Board of Supervisors of Louisiana State University; Agricultural and Mechanical College, both of Baton Rouge, La.

[21] Appl. No.: 123,613

[22] Filed: Sep. 16, 1993

[51] Int. Cl.$^6$ .................. A01N 59/00; A01N 59/08; A01N 43/38; A01N 43/40

[52] U.S. Cl. .................... 424/661; 424/600; 424/617; 424/662; 424/663; 424/664; 424/665; 424/679; 424/722; 424/723; 210/749; 210/764; 514/253; 514/255; 514/415; 514/635; 514/649

[58] Field of Search ............ 424/600, 617, 661, 662, 424/663, 664, 665, 679, 722, 723; 210/749, 764; 514/415, 253, 255, 649, 635

[56] References Cited

U.S. PATENT DOCUMENTS

| | | | |
|---|---|---|---|
| 4,447,411 | 5/1984 | Langdon | 424/14 |
| 5,017,620 | 5/1991 | Grassman et al. | 514/698 |
| 5,366,975 | 11/1994 | Nathanson | 514/255 |

OTHER PUBLICATIONS

S. W. Fisher et al., "Molluscicidal activity of potassium to the zebra mussel *Dreissena polymorpha*: Toxicity and mode of action," Aquatic Toxicol., vol. 20, pp. 219–234 (1991).

J. Horohov et al., "Ion transport in the freshwater zebra mussel, *Dreissena polymorpha*," Biol. Bull., vol. 183, pp. 297–303 (1992).

T. H. Dietz et al., "Potassium and rubidium uptake in freshwater mussels," J. Exp. Biol., vol. 150, pp. 395–405 (1990).

J. L. Ram et al., "Chemical Regulation of spawning in the zebra mussel *Dreissen polymorpha*)" in T. F. Nalepa et al. (eds.) *Zebra Mussel: Biology, Impacts, and Control* (1993).

D. B. Gardiner et al., "Musculature associated with the water canals in freshwater mussels and response to monoamines in vitro," Biol.Bull., vol. 180, pp. 453–465 (1991).

T. H. Dietz et al., "Monoamine transmitters and cAMP stimulation of Na transport in freshwater mussels," Can. J. Zool., vol. 60, pp. 1408–1411 (1982).

D. B. Gardiner et al., "Long-Term Culture of Freshwater Mussel Gill Strips: Use of Serotonin to Affect Aseptic Conditions," Biol. Bull., vol. 181, pp. 175–180. (1991).

H. Silverman et al., "Gill structure and it possible relationship to filtration mechanics in *Dreissena polymorpha*," poster presented at the Third International Zebra Muussel Conference, Toronto (Feb. 25, 1993).

*Primary Examiner*—Allen J. Robinson
*Assistant Examiner*—John D. Pak
*Attorney, Agent, or Firm*—John H. Runnels

[57] ABSTRACT

A method for enhancing the effect of a toxicant such as chlorine or potassium on bivalve molluscs such as zebra mussels. Application of serotonin or a serotonin agonist in low concentrations inhibits the mussels' ability to close their valves to protect themselves from the effect of any toxicants in the water. Thus administering serotonin or a serotonin agonist for a period of time, followed by administering a toxicant, substantially enhances the effect of the toxicant on the zebra mussels. Thus less of the toxicant need be administered to control zebra mussels. The concentration of serotonin needed to enhance toxicant control of exotic zebra mussels has been found to be at or below the threshold of serotonin activity on native bivalves, at least those native to the lower Mississippi River. Furthermore, serotonin is naturally degraded rapidly by aquatic microorganisms. Thus the serotonin itself is environmentally benign; and it allows the use of toxicants at lower levels than otherwise could be used, reducing any environmental impact of the toxicants. Serotonin agonists such as trifluoromethylphenylpiperazine may be used in place of serotonin.

24 Claims, No Drawings

METHOD FOR CONTROLLING BIVALVES SUCH AS ZEBRA MUSSELS

This invention pertains to a method for controlling freshwater bivalves such as zebra mussels, particularly to a method for enhancing the effect of toxicants on zebra mussels.

The zebra mussel, *Dreissena polymorpha*, is a freshwater clam native to the Caspian Sea. It has been introduced as an unwanted exotic species in freshwater bodies of water in Europe, and more recently in North America. In a favorable environment, zebra mussel populations can grow in a seemingly unrestrained manner, which can cause numerous problems. Population densities can reach $10^5/m^2$. Thick layers of the clams can clog pipes and machinery in power plants and industrial plants located on infested bodies of water, resulting in expensive plant shutdowns and expensive removal procedures. The zebra mussels can also adhere to the undersides of vessels, causing increased hydraulic drag, and again resulting in lost time and expense in removing the shells.

Control of zebra mussels has become critically important to municipalities, industrial plants, and power plants located on the Great Lakes, and, more recently, on some of the major river systems in the United States, including the Ohio, Tennessee, and Mississippi Rivers. The main control strategies which have been used to date are the mechanical scraping of fouled facilities, and the chlorination of water to prevent fouling. Chlorination has previously been effective in controlling zebra mussels only if used more-or-less constantly, and at relatively high concentrations. EPA regulations require the removal of chlorine from treated water before the water is returned to the lake or water from which it was drawn. The expense of chlorine removal may exceed the cost of the chlorine itself.

Zebra mussels are relatively intolerant of major changes in water ion concentrations, particularly potassium, and are also sensitive to the addition of elemental chlorine (usually delivered as residual chlorine in the 1 ppm range). See S. W. Fisher et al., "Molluscicidal activity of potassium to the zebra mussel *Dreissena polymorpha*: Toxicity and mode of action," Aquatic Toxicol., vol. 20, pp. 219–234 (1991); and J. Horohov et al., "Ion transport in the freshwater zebra mussel, *Dreissena polymorpha*," Biol. Bull., vol. 183, pp. 297–303 (1992). See also T. H. Dietz et al., "Potassium and rubidium uptake in freshwater mussels," J. Exp. Biol., vol. 150, pp. 395–405 (1990).

Serotonin, a neurotransmitter, is an amino acid derivative, 5-hydroxytryptamine. T. H. Dietz et al., "Monoamine transmitters and cAMP stimulation of Na transport in freshwater mussels," Can. J. Zool., vol. 60, pp. 1408–1411 (1982) discussed the effect of serotonin on increased sodium transport in unionid mussels. D. B. Gardiner et al., "Musculature associated with the water canals in freshwater mussels and response to monoamines in vitro," Biol. Bull., vol. 180, pp. 453–465 (1991) disclosed that serotonin causes musculature in the gill of freshwater mussels to relax, resulting in greater than normal water flow. Other investigators have also shown that exogenous serotonin application will cause the spawning of gametes in a variety of mussels, including the spawning of gametes from male zebra mussels. See, e.g., J. L. Ram et al., "Chemical regulation of spawning in the zebra mussel (*Dreissena polymorpha*)" in T. F. Nalepa et al. (eds.) *Zebra Mussel: Biology, Impacts, and Control* (1993).

There remains an unfilled need for easy and effective methods of controlling unwanted zebra mussel or other freshwater bivalve populations, such as the Asian clam, *Corbicula fluminea*.

It has been discovered that exposing freshwater bivalves such as zebra mussels to certain neurotransmitters such as serotonin enhances the effect of toxicants on the bivalve. Upon exposure to a toxicant, the normal behavior of mussels is valve closure and reduction of water movement across the gills of the animal. The effective dose at which a toxicant becomes lethal to the animal thus becomes a combination both of the lethality of the toxicant, and of the animal's ability to avoid exposure to the toxicant. We have discovered a novel method for reducing the animal's ability to avoid such exposure. As one example, exogenous application of serotonin, a potent neurotransmitter, has been found to greatly inhibit the animal's ability to respond to the noxious stimulus of a toxicant. Thus less toxicant may be used to control zebra mussel infestations.

Serotonin has neurotransmitter effects on mussels. Our observation of mussels, including zebra mussels, indicated that after exposure to serotonin the mussels exhibited valve gaping activity. Our experiments have shown that: (1) zebra mussel gill ciliary activity was increased by exogenous application of serotonin; (2) zebra mussel gill musculature was relaxed by serotonin; (3) valve gaping and, occasionally, foot extension were stimulated by serotonin, even in the presence of toxic levels of chlorine or potassium; and (4) this behavior resulted in reduced survivability of mussels exposed to toxic agents. Thus pre-treatment of mussels with serotonin causes them to be more susceptible to toxins.

Serotonin, a neurotransmitter, acts as an excitatory agent for the pumping of water through the animals. Following exposure to serotonin, zebra mussels will continue to move water containing noxious or toxic materials over their bodies. The protective reflexes of the animals, which would normally cause the shells to close, become inoperative. In addition, settling zebra mussel larvae are also affected by serotonin. Because both settling veliger larvae and adult mussels are susceptible to the novel treatment, the need for constant chlorination is eliminated through this invention. Treatments may now be made intermittently as needed. For example, it will be preferable to treat more frequently during peak larval and attachment periods, early spring through late fall, often curtailing somewhat during hot weather in the summer. Treatments may be made either more-or-less continuously—alternately applying lower concentrations of serotonin and toxicant; or discontinuously applying higher concentrations.

We have found that serotonin agonists which bind to a number of different specific tissue binding sites are also effective in eliciting behavior similar to that caused by serotonin. In addition, we have found that the larval veliger stages of the mussel are also susceptible to behavioral modifications caused by serotonin. For each of these reasons, serotonin pretreatment enhances the ability of toxicants to control zebra mussel populations.

Animal collection and storage

Zebra mussels, *Dreissena polymorpha*, were collected either in Michigan from Lake Erie at the mouth of the Raisin River, or from the Mississippi River near Baton Rouge, La. The animals were stored in the laboratory in aerated artificial pondwater (PW) (0.5 mM NaCl, 0.4 mM CaCl$_2$, 0.2 mM MgSO$_4$, 0.2 mM NaHCO$_3$, 0.05 mM KCl). For long-term storage, the animals were held at 8° C. All mussels held at 8° C. were transferred to a 16° C. environment for 5 days or more before being acclimated to room temperature.

Serotonin or serotonin agonist treatment, and behavioral observation

Zebra mussels were carefully detached from their attachment sites by cutting byssal threads (instead of pulling them free). This procedure avoids damage to the foot and other internal organs. The mussels were placed in pondwater containing the test agent. All agents were tested at a concentration of $10^{-4}$ M (which for serotonin is equivalent to 40.5 ppm).

In the animal kingdom, there are several specific receptors in tissue that bind serotonin. Six of those sites are denoted as 5HT$_1$, 5HT$_{1A}$, 5HT$_{1B}$, 5HT$_{1C}$, 5HT$_2$, and 5HT$_3$. We tested four serotonin agonists specific for these identified sites. The compounds tested were buspirone, trifluoro-methylphenylpiperazine (TFMPP), dimethoxy-4-iodophenyl-2-aminopropane (DOI), and 1-m-chlorophenyl biguanide (CPB).

Following exposure to these compounds, the animals' behavior was observed for several hours. Animals were observed for undisturbed valve gape, closure of valves following mechanical disturbance, and time to reopening of valves following disturbance. The mechanical disturbance consisted of lightly tapping on the beaker containing a clam. Observations were scored on the following arbitrary scale: —no effect; +open valves, normal valve closure response when disturbed; + +wider valve gape but normal response to mechanical disturbance; + + +extreme valve gape without full valve closure on disturbance.

Serotonin enhancement of chlorine and potassium toxicity

Adult zebra mussels were transferred to PW. Half the animals received a single exposure to $10^{-4}$ M serotonin for 30 min. Chlorine bleach (5.25% nominal concentration) was mixed with aerated pondwater in a glass container to yield a 5 ppm initial nominal chlorine concentration. The actual chlorine concentration was less than the nominal concentration because of interactions with the container, with the water, and with organic matter associated with a zebra mussel placed in the solution. The PW solution, with or without chlorine, was siphoned into all-glass, 300 ml containers. One or two mussels were placed into each of the containers. All containers were sealed for approximately 24 hr, after which the solution was replaced by fresh PW or by PW+chlorine. The treatment conditions were as follows: PW; PW+serotonin pre-treatment; PW+chlorine; or PW+serotonin pre-treatment+chlorine. Animals were examined at regular intervals, and it was noted whether valves were open or closed. The valves or mantle edges were mechanically stimulated by manipulating a magnet under the container to cause a magnetic, teflon-coated bar inside the container to contact the animal. (The container remained sealed.) Animals that remained opened when mechanically disturbed were recorded as being dead.

Similar procedures were followed to determine whether serotonin enhanced the toxic effects of elevated potassium levels. Adult zebra mussels were pre-treated with serotonin for 30 min. The animals were then transferred to PW with additional KCl ($10^{-3}$ M, 35 ppm K). Data were collected as described above for chlorine.

Microscopic observation of serotonin's effect on gill ciliary activity and on veliger behavior In preparation for microscopic analysis, gills were carefully dissected from zebra mussels and then kept in pondwater until observation. Gill ciliary activity was observed either with an inverted light microscope, or with a laser confocal microscope. A strip of living gill material was placed on a microscope slide, and a coverslip was suspended over the tissue using petroleum jelly to create an open ended channel including the gill. Serotonin was applied directly to the living tissue by using a wick to move fluid under the coverslip. Video tape recordings of the cilia were made to study their response to serotonin treatment at various concentrations from $10^{-8}$ M to $10^{-3}$ M. Contraction and relaxation of the underlying gill musculature could also be observed with these preparations. In addition, some gills were fixed to allow observation of the ostia. Gill strips were placed in 2% glutaraldehyde in 30 mosM phosphate buffer, pH 7.2, post-fixed in 1% osmium tetroxide and dehydrated in an acetone series. Some of these gill strips were teased apart to allow observation of ostia. See generally D. B. Gardiner et al., "Long-Term Culture of Freshwater Mussel Gill Strips: Use of Serotonin to Affect Aseptic Conditions," Biol. Bull., vol. 181, pp. 175–180 (1991).

Veliger larvae were also observed microscopically after treatment with serotonin. Veliger larvae of zebra mussels were collected with a plankton net, and were used within 1–3 days of collection. The cilia on the velum swimming organ of the larvae were visible microscopically through the transparent shell. Ciliary movement experiments were recorded on video tape.

General effects of serotonin on the zebra mussels.

Serotonin treatment dramatically altered the behavior of veliger larvae. Serotonin consistently stimulated the activity of the cilia associated with the velum swimming organ. An initial effect was noted at a serotonin concentration of $10^{-8}$ M (4 parts per billion, ppb). Maximum ciliary activity was elicited at serotonin concentrations between $10^{-6}$ and $10^{-5}$ M.

Veliger larvae exposed to serotonin also exhibited valve gaping behavior, Valve musculature was apparently relaxed by serotonin, allowing the shells to open. The larvae intermittently closed their valves, but the valves usually reopened quickly. Sustained valve gaping was evident at $10^{-6}$ M serotonin.

Adult gill cilia showed much the same response as velum cilia to serotonin exposure. A concentration of about $10^{-8}$ M serotonin appeared to be the threshold for increased ciliary activity, and maximum response was obtained between $10^{-6}$ and $10^{-4}$ M serotonin. At the latter concentrations, musculature in the gill was also relaxed. The combination of increased ciliary activity and a wide-open gill water canal system is believed to result in maximum water flow through a mussel.

When adult zebra mussels were challenged with $10^{-4}$ M serotonin in the PW, they consistently gaped their valves. If mechanically disturbed, the valves would close only partially, and then rapidly reopen. When serotonin-treated zebra mussels were exposed to noxious or toxic chemicals (e.g., glutaraldehyde, chlorine, and K$^+$) which would otherwise normally cause the valves to close, the mussels instead tended to leave their valves open at least intermittently, as discussed further below.

Serotonin enhancement of the lethal effect of chlorine

Animals were pre-treated with $10^{-4}$ M serotonin, and were then exposed either to 5 ppm chlorine in pondwater, or to pondwater containing no unreduced chlorine. The results of a representative experiment are shown in Table 1.

TABLE 1

| Treatment (days) | $LT_{50}$ (days) | $LT_{100}$ (days) |
|---|---|---|
| PW | no deaths | |
| PW + choline | 2.6 | 3.9 |
| PW + serotonin | no deaths | |
| PW + serotonin + chlorine | 0.6 | 2.9 |

Table 1 indicates the time taken for half the animals in a treatment group to die ($LT_{50}$) and the time taken for all animals to die ($LT_{100}$). Each individual experiment contained a total of ten animals in each group. Pre-treatment with serotonin enhanced the effect of the chlorine alone, causing survival times following chlorine exposure to drop dramatically. These experimental results have been duplicated in subsequent experiments (data not shown).

Of interest in warmer areas such as the lower Mississippi River is the effect of higher water temperature on these results. Table 2 gives results for a representative experiment run with a group of animals which were first acclimated to a temperature of 27°–30° C. for six weeks.

TABLE 2

| Treatment | $LT_{50}$ (days) | $LT_{100}$ (days) |
|---|---|---|
| PW | no deaths | |
| PW + choline | 0.28 | 0.87 |
| PW + serotonin | no deaths | |
| PW + serotonin + chlorine | 0.16 | 0.50 |

The animals in warmer water were more sensitive to chlorine in general. This effect was dramatically enhanced by serotonin pre-treatment. In the field, the enhancing effect of serotonin may be greater at warmer temperatures, because the effects of a single exposure to serotonin typically last for only a few hours.

Serotonin enhancement of potassium toxicity

To test whether the effect of serotonin was chlorine-specific or applied to toxicants more generally, a similar set of experiments was run at elevated potassium concentrations. Table 3 gives the results of these experiments.

TABLE 3

| Treatment | $LT_{50}$ (days) | $LT_{100}$ (days) |
|---|---|---|
| PW | (15% death 19 days) | ND |
| PW + KCl | 2.5 | 19 |
| PW + serotonin | (25% death 19 days) | ND |
| PW + serotonin + KCl | 0.88 | 6.6 |

Potassium salts (e.g., KCl) have previously been demonstrated to be lethal to all freshwater bivalves examined to date. Serotonin causes zebra mussels to open their valves, increasing the exposure of the animal to any noxious or toxic chemicals in the environment. The result is to hasten the effectiveness of the killing agent, regardless of the identity of the particular killing agent.

Toxicants which may also be useful in practicing the present invention include bromine, or a combination of bromine and chlorine.

Serotonin Agonists

Because serotonin effectively enhances the lethality of zebra mussel toxicants, it is expected that other pharmaceutical agents which are serotonin agonists will have the same effect. A "serotonin agonist" is a compound or composition having substantially the same pharmaceutical activity as serotonin on a zebra mussel or other mollusc. Such an agonist may or may not possess structural similarity to serotonin. Such agonists include, for example, those listed in Table 4 below. Analogs or modifications of the listed compounds that will occur to one of skill in the art will often be serotonin agonists as well.

TABLE 4

| Serotonergic Agonists | | |
|---|---|---|
| Name | Abbreviation | Selectivity |
| 8-[2-[4-(2-methoxyphenyl)-1-piperazinyl]ethyl]-8-azaspirol[4,5]decane-7,9-dione dihydrochloride | BMY7378 | $5HT_{1A}$ |
| 3-[2-(dimethylamino)ethyl]-1H-indol-5-ol oxalate | Bufotenine monooxalate | 5HT |
| 8-[4-[4-(2-pyrimidinyl)-1-piperazinyl]butyl]-8-azaspiro[4,5]decane-7,9-dione HCl | Buspirone HCl | $5HT_{1A}$ |
| 3-(2-aminoethyl)-1H-indol-5-carboxamide maleate | 5-Carboxamidotryptamine maleate (5-CT) | $5HT_{1A}$ |
| N-(3-chlorophenyl)imidodicarbonimidic diamide HCl | 1-(m-chlorophenyl)-biguanide HCl | $5HT_3$ |
| 1-(3-chlorophenyl)piperazine HCl | m-CPP diHCl | $5HT_1$ |
| 7-trifluoromethyl-4(4-methyl-1-piperazinyl)-pyrolo[1,2-a]quinoxaline, 1:2 maleate salt | CGS-12066B maleate | $5HT_{1B}$ |
| 3-(N,N-dipropylaminoethyl)-1H-indol-5-carboxamide maleate | dipropyl-5CT | $5HT_{1A}$ |
| (±)-1-(2,5-dimethoxy-4-iodophenyl)-2-aminopropane | HCl DOI HCl | $5HT_2/5HT_{1C}$ |
| (±)-1-(4-bromo-2,5-dimethoxyphenyl)-2-aminopropane | HCl DOB HCl | $5HT_2/5HT_{1C}$ |
| 1-(2,5-dimethoxyphenyl)-2-aminopropane HCl | DMA HCl | 5HT |
| N,N,N-trimethylserotonin iodide | 5-HTQ iodide | $5HT_3$ |
| (±)-8-hydroxydipropylaminotetralin HBr | ±8-OH-DPAT (or purified + or − forms) | $5HT_{1A}$ |
| 9,10-didehydro-N,N-diethyl-6-methylergoline-8β-carboxamide, D-tartrate | Delysid | 5HT |
| 5-methoxy-N,N-dimethyltryptamine hydrogen oxalate | 5-Ome DMT oxalate | 5HT |
| 1-(2-methoxyphenyl)piperazine HCl | 5-MMP HCl | $5HT_1$ |
| 5-methoxytryptamine HCl | O-me 5HT | 5HT |
| 3-(2-aminoethyl)-2-methyl-1H-indol-5-ol maleate | 2-me 5HT | $5HT_3$ |
| (±)-3-(2-aminopropyl)-indol-5-ol maleate | α-me 5HT | $5HT_2$ |
| p-aminophenylethyl-m-trifluoromethylphenyl piperazine | PAPP | $5HT_{1A}$ |

TABLE 4-continued

| Serotonergic Agonists | | |
|---|---|---|
| Name | Abbreviation | Selectivity |
| N-phenyl-imidocarbonimidic diamide | 1-phenylbiguanide | $5HT_3$ |
| 2-(1-piperazinyl)quinoline dimaleate | Quipazine dimaleate | 5HT |
| 2-[1-(4-methyl)-piperazinyl] quinoline dimaleate | Quipazine, N-me dimaleate | $5HT_{1B}$ |
| 5-hydroxytryptamine creatinine sulfate | Serotonin (or 5HT) | 5HT |
| 5-hydroxytryptamine HCl | Serotonin (or 5HT) | 5HT |
| 5-hydroxytryptamine oxalate salt | Serotonin (or 5HT) | 5HT |
| (±)-8-[(2,3-dihydro-1,4-benzodioxin-2-yl)methyl]-1-phenyl-1,3,8-triazaspirol[4,5]decan-4-one | Spiroxatrine | $5HT_{1A}$ |
| m-trifluoromethylphenylpiperazine HCl | TFMPP HCl | 5HT |
| 6[[3-[4-(o-methoxyphenyl)-1-piperazinyl]propyl]amino]-1,3-dimethyluracil HCl | Urapidil HCl | $5HT_{1A}$ |
| 5-methyl-6[[3-(4-(2-methoxyphenyl)-1-piperazinyl]propyl]amino]-1,3-dimethyluracil | Urapidil, 5-me | $5HT_{1A}$ |
| 2-(2,6-dimethoxyphenoxyethyl)aminomethyl-1,4-benzodioxane HCl | WB-4101 HCl | $5HT_{1A}$ |

Preliminary experiments with several of these serotonin agonists to determine their effect on the mussels' behavior supports the conclusion that serotonin agonists will also be effective in practicing the method of this invention. These results are summarized in Table 5.

TABLE 5

| Agonist | Specificity | Effects |
|---|---|---|
| PW only | — | + |
| Serotonin (5HT) | all receptors | +++ |
| Buspirone | $5HT_{1A}$ | +++ |
| Trifluoromethylphenylpiperazine (TFMPP) | $5HT_{1B}$ | +++* |
| Dimethoxy-4-iodophenyl-2-aminopropane (DOI) | $5HT_{1C}/5HT_2$ | ++ |
| 1-m-chlorophenyl biguanide (CPB) | $5HT_3$ | ++ | ps +normally open valves; ++wider valve gape but normal valve closure response to mechanical disturbance; +++extreme valve gape and not fully closing when disturbed; * caused release of gametes from the gonad (both sperm and eggs) and 24 hr of exposure causes damage to epithelia with the loss of some ciliated cells (likely due to prolonged, excessive ciliary activity). Based on these results, trifluoromethylphenylpiperazine (TFMPP) is believed to be a particularly promising candidate for use in the methods of this invention. The above data also suggests that agonists in classes $5HT_{1A}$ or $5HT_{1B}$ may generally be more effective. The more formal chemical name for TFMPP is 1-[3-(trifluoromethyl)phenyl]-piperazine.

Serotonin alone temporarily causes the mussel to lose nervous system control over various motor behaviors. Serotonin, at the concentrations tested, is not itself a lethal agent. Rather, serotonin causes a loss of the animal's normal protective responses, enhancing contact with any toxic agent in the environment, leading to more rapid death of the mussel.

Serotonin and its agonists (especially those in receptor class 1) cause behavioral and physiological responses which tend to increase water flow through the animal. This response leads to an enhanced susceptibility to toxicants. Behavioral changes in the larvae have also been demonstrated. It is expected that these larval behavioral changes will inhibit or prevent their normal settling.

Industrial control of zebra mussels has often relied on chlorine treatment(s). By extrapolating the above results, it is expected that the following strategy for field use of serotonin or its agonists will enhance the toxicity of chlorine (or other toxicant): A single exposure to serotonin causes an effect lasting only for a few hours. Thus following a single serotonin exposure a toxicant should exert its maximum effect during the first few hours. The effectiveness of administering serotonin in the field should be greater if the serotonin is continuously applied, preferably for less than an hour, and then its application is discontinued. Then the toxicant should be administered.

Zebra mussel larvae respond near-maximally to $10^{-6}$ M serotonin concentration. This concentration is near or below the threshold for any effect in native bivalves we have studied in the lower Mississippi region; administration at this concentration may allow native bivalves to conduct normal protective behaviors when confronted with toxicants. At $10^{-6}$ M serotonin, zebra mussels will be more specifically affected by the toxicant. The toxicant will be administered for several hours, and then discontinued after the maximum toxic effect is reached. The toxicant is preferably monitored continuously, and its application is adjusted to maintain the concentration desired. For example, in the lower Mississippi River about 4 ppm chlorine usually must be administered to achieve 0.5 ppm residual chlorine after the chlorine reacts with oxidizable materials naturally present in the river water. Several hours after terminating the toxicant treatment, the cycle of serotonin followed by toxicant may be repeated as many times as needed to remove substantially all of veliger larvae from the water; the treatment cycle as a whole may need to be repeated after a passage of time, the specific time depending on local circumstances.

A preferred procedure designed to have optimal effect on a zebra mussel population is as follows:
1. Inject serotonin or other agonist at an initial dose of $10^{-6}$ M for a 30 minute treatment time. This concentration is equivalent to 1.75 lb of serotonin creatine sulfate complex per million gallons of water treated. Chemical analysis may help determine the degree of any spontaneous degradation of serotonin, with the dosage adjusted accordingly.
2. Following serotonin treatment, initiate injection of toxicant at the desired dose. Treatment should be continued for a few hours, and then discontinued after about 3-5 hours. After a 6-12 hour recovery period, the sequence may be repeated as needed.

Following this protocol will substantially reduce the total amount of chlorine or other toxicant needed to control an infestation. Preliminary calculations suggest, for example, that if chlorine is used as a toxicant, the amount of chlorine needed to successfully control zebra mussels in the lower Mississippi River may be reduced by about half. The addition of serotonin at the levels indicated should be both safe and environmentally sound, considering that serotonin is a natural product that will be eliminated quickly by aquatic microorganisms with no long-term adverse effects. Thus the serotonin itself is environmentally benign; and it allows the use of toxicants at lower levels and for shorter durations than otherwise could be used, reducing both the cost and any environmental impact of the toxicants. Furthermore, serotonin is rapidly oxidized in raw water, and would, for example, be completely oxidized by chlorine if chlorine were used as the toxicant following the serotonin administration. Thus it is particularly important to administer serotonin and the toxicant sequentially where the toxicant, such as chlorine, is able to oxidize serotonin.

Although the examples given above used the zebra mussel, those of skill in the art will appreciate that the techniques of this invention may be readily adapted to enhance the control of other freshwater bivalve molluscs as well. As noted, the zebra mussel is more sensitive to serotonin than are many other bivalves; however, by adjusting the concentration of serotonin or other agonist used, the methods of the present invention are expected to enhance generally the effect of toxicants on other bivalve molluscs, and perhaps gastropod molluscs as well. In particular, it is expected that the techniques of the present invention will be useful in controlling another freshwater bivalve pest species, the Asian clam, *Corbicula fluminea*.

The complete disclosures of all references cited in this specification are hereby incorporated by reference.

We claim:

1. A method of controlling a freshwater bivalve population of the genus Dreissena, comprising the steps of:
    (a) treating the water populated by the bivalves with an aqueous solution of a compound, for a time and at a concentration sufficient to substantially inhibit the ability of at least some of the bivalves to close their valves; wherein the compound is selected from the group consisting of: (i) serotonin; (ii) 8-[4-[4-(2-pyrimidinyl)-1-piperazinyl]butyl]-8-azaspiro[4,5]decane-7,9-dione; (iii) 1-[3-(trifluoromethyl)phenyl]-piperazine; (iv) 1-(2,5-dimethoxy-4-iodophenyl)-2-aminopropane; and (v) N-(3-chlorophenyl)imidodicarbonimidic diamide; and
    (b) treating the bivalves with a toxicant, for a time and at a concentration sufficient to kill at least some of the bivalves whose ability to close their valves has been substantially inhibited by said compound.

2. A method as recited in claim 1, wherein said compound is serotonin.

3. A method as recited in claim 1, wherein said compound is 1-[3-(trifluoromethyl)phenyl]-piperazine.

4. A method as recited in claim 1, wherein said compound is 8-[4-[4-(2-pyrimidinyl)-1-piperazinyl]butyl]-8-azaspiro[4,5]decane-7,9-dione.

5. A method as recited in claim 1, wherein said compound is 1-(2,5-dimethoxy-4-iodophenyl)-2-aminopropane.

6. A method as recited in claim 1, wherein said compound is N-(3-chlorophenyl)imidodicarbonimidic diamide.

7. A method as recited in claim 1, wherein the toxicant is selected from the group consisting of unreduced chlorine, unreduced bromine, and potassium ions.

8. A method as recited in claim 1, wherein said compound is serotonin, and wherein the toxicant comprises unreduced chlorine.

9. A method as recited in claim 1, wherein said compound is 1-[3-(trifluoromethyl)phenyl]-piperazine, and wherein the toxicant comprises unreduced chlorine.

10. A method as recited in claim 1, wherein the bivalve population comprises Dreissena larvae, and wherein the method additionally comprises repeating each of the steps of the method of claim 1 until substantially all the larvae are killed.

11. A method as recited in claim 1, wherein the freshwater bivalve population comprises a population of *Dreissena polymorpha*.

12. A method as recited in claim 11, wherein said compound is serotonin.

13. A method as recited in claim 11, wherein said compound is 1-[3-(trifluoromethyl)phenyl]-piperazine.

14. A method as recited in claim 11 wherein said compound is 8-[4-[4-(2-pyrimidinyl)-1-piperazinyl]butyl]-8-azaspiro[4,5]decane-7,9-dione.

15. A method as recited in claim 11, wherein said compound is 1-(2,5-dimethoxy-4-iodophenyl)-2-aminopropane.

16. A method as recited in claim 11, wherein said compound is N-(3-chlorophenyl)imidodicarbonimidic diamide.

17. A method as recited in claim 11, wherein the toxicant is selected from the group consisting of unreduced chlorine, unreduced bromine, and potassium ions.

18. A method as recited in claim 11, wherein said compound is serotonin, and wherein the toxicant comprises unreduced chlorine.

19. A method as recited in claim 11, wherein said compound is 1-[3-(trifluoromethyl)phenyl]-piperazine, and wherein the toxicant comprises unreduced chlorine.

20. A method as recited in claim 11, wherein the *Dreissena polymorpha* population comprises *Dreissena polymorpha* larvae, and wherein the method additionally comprises repeating each of the steps of the method of claim 11 until substantially all the larvae are killed.

21. A method as recited in claim 1, wherein said treating with the aqueous solution of said compound comprises treating with serotonin at a concentration between about $10^{-8}$ M and about $10^{-3}$ M, for a period of at least ten minutes.

22. A method as recited in claim 21, wherein said treating with the aqueous solution of said compound comprises treating with serotonin at a concentration between about $10^{-6}$ M and about $10^{-4}$ M, for a period of about thirty minutes.

23. A method as recited in claim 1, wherein said treating with the aqueous solution of said compound comprises treating with 1-[3-(trifluoromethyl)phenyl]-piperazine at a concentration between about $10^{-8}$ M and about $10^{-3}$ M, for a period of at least ten minutes.

24. A method as recited in claim 23, wherein said treating with the aqueous solution of said compound comprises treating with 1-[3-(trifluoromethyl)phenyl]-piperazine at a concentration between about $10^{-6}$ M and about $10^{-4}$ M, for a period of about thirty minutes.

* * * * *